United States Patent [19]
Maruya et al.

[11] Patent Number: 4,749,719
[45] Date of Patent: Jun. 7, 1988

[54] METHOD OF TREATING SKIN PIGMENTATION ABNORMALITIES WITH PANTETHEINE-S-SULFONIC ACID

[75] Inventors: Yoshiji Maruya, Tokyo; Toshio Taki, Kanagawa, both of Japan

[73] Assignee: Sogo Pharmaceutical Company Limited, Tokyo, Japan

[21] Appl. No.: 829,546

[22] Filed: Feb. 13, 1986

Related U.S. Application Data

[62] Division of Ser. No. 650,064, Sep. 13, 1984, abandoned.

[30] Foreign Application Priority Data

Sep. 21, 1983 [JP] Japan .................. 58-173077

[51] Int. Cl.$^4$ ........................................... A61K 31/185
[52] U.S. Cl. .................................................. 514/517
[58] Field of Search ........................................ 514/517

[56] References Cited

U.S. PATENT DOCUMENTS 3,803,119  4/1974  Tamura et al. .................. 260/112.5
3,876,799  4/1975  Tamura et al. ...................... 514/517

FOREIGN PATENT DOCUMENTS 58-4721  1/1983  Japan .

OTHER PUBLICATIONS

Hayakawa et al., Acta Vitaminol Enzymol., I, 109 (1985).
Nakamura, H. et al, "Growth Responses of *Bifidobacterium bifidum* to S-Sulfonic Acid-Type Pantetheine Related Compounds" *Japan. J. Microbiol.* vol. 16 (2) 239-242 (1972).
Kopelevich, V. M. et al, "Research of Acyl Group Carriers. XIII New Method of Synthesis of D-(+-)-S-Sulfopantetheine and its Conversion to Coenzyme Forms of Vitamin $B_3$ in Animals" *Khim.Farm.Zh.*, vol. 12 (8), pp. 72-75 (1978).
Moiseenok, A. G. et al "Antiinflammatory and Coenzyme Activity of Pantothenic Acid Derivatives in Adjuvant Arthritis", *Khim. Farm. Zh.*, vol. 15(6), pp. 76-81 (1981).

*Primary Examiner*—Nicky Chan
*Attorney, Agent, or Firm*—Browdy & Neimark

[57] ABSTRACT

Pantetheine-S-sulfonic acid and/or its salt(s) have(has) an effect of curing and preventing pigmentation in the skin, an effect of improving rough skin and a curative effect to wounds, burns and the like, therefore being used for agents for epidermis.

1 Claim, 1 Drawing Sheet

METHOD OF TREATING SKIN PIGMENTATION ABNORMALITIES WITH PANTETHEINE-S-SULFONIC ACID

This application is a division of application Ser. No. 650,064, filed Sept. 13, 1984, now abandoned.

This invention relates to a dermatological preparation, and, more specifically, to an external preparation for application to skin containing pantetheine-S-sulfonic acid and/or its salt, as a medical base, which preparation not only has an excellent curative and preventative effect but also causes a good feeling upon use and is able to be stored over a long period of time.

It is known that pantetheine-S-sulfonic acid and its salts are useful as a precursors of coenzyme A which plays an important role in energy metabolism, lipid metabolism and acetylation (Japan J. Microbiol vol 16 (3) 239~242 (1972) ). However, there are no experiences in which these compounds were used for external preparations for application to skin or suggesting the superior curative and preventive effect of said preparation on pigmentation.

Skin troubles include those such as burns and wounds in which tissue is directly damaged, thereby causing a direct hindrance to the maintenance of health, and those involving pigmentation and coloration which cause problems in the appearance although not hindering the maintenance of health, thereby directly causing social impediments. For women especially, so-called blemishes are a serious problem in terms of both beauty and health. It is said that a considerably large proportion of the middle-aged and elderly women are actually suffering from blemishes. Conventionally, stress was placed on the prevention and treatment of the former troubles and minimal consideration was given to the latter troubles. However, in accordance with the recent changes in social conditions, the latter troubles also have come to be highlighted and studied. For instance, external preparations containing hydrogen peroxide, ascorbic acid, colloidal sulfur and the like are used for the treatment and prevention of the latter troubles. However, it is hard to say that these materials are excellent due to their low stability, bad smell and inconvenience in handling as well as in terms of practical effect. Accordingly it has been an urgent technical subject in this art to establish a superior external preparation for application to skin containing a material other than the above materials.

After screening a number of materials which were collected from various fields and which comprised various organic and inorganic matters as well as compounds of known or unknown structures, special attention came to be paid to pantothenic acid. After that, as the result of further investigation of pantothenic-acid-system compounds, it was newly found that pantetheine-S-sulfonic acid has a remarkable effect in the treatment of pigmentation abnormalities in the skin which is based on its tyrosinase-activity inhibiting effect and that it has an effect of improving the quality of skin such as rough skin through improvement and control of skin metabolism. In addition, it was confirmed that pantetheine-S-sulfonic acid causes an excellent curative effect to wounds, burns and the like leading to a conviction that this compound can be very effectively used for an external preparation for application to skin, thereby completing this invention.

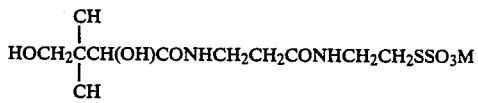

Figure 1:
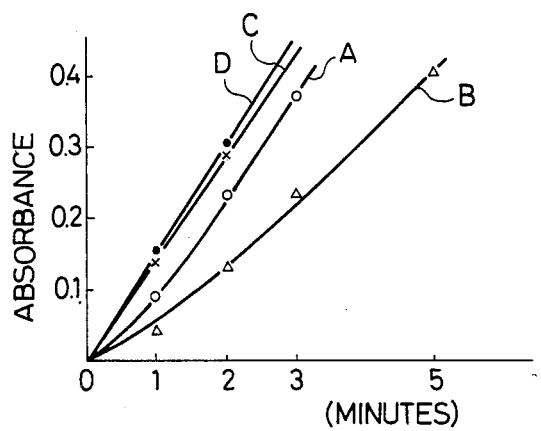
FIG. 1 indicates that calcium pantetheine-S-sulfonate exhibited a superior tyrosinase-activity inhibiting effect in experiment 1.
A: test solution A,
B: test solution B
C: reference solution B,
D: blank In FIG. 2, the clinical effects of creamy external preparations containing 10% and 0% calcium pantetheine-S-sulfonate on liver spot are represented by successive changes in the mean level of color difference.
a: external preparation containing 10% calcium pantetheine-S-sulfonate
b: external preparation containing 0% calcium pantetheine-S-sulfonate Pantetheine-S-sulfonic acid or its salt is a well-known compound represented by the following formula.

(In the formula, M represents hydrogen, an alkali metal or ½ alkaline earth metal.) There are no problems in the supply of the effective component because this compound is now able to be mass-produced easily from, for example, D-pantothenic acid and 2-aminoethanethiolsulfuric acid.

Pantethine and pantetheine are listed as compounds relatively similar to pantetheine-S-sulfonic acid although they have various disadvantages for external preparations for application to skin. That is to say, pantetheine causes much inconvenience in handling due to its noncrystallinity and viscosity. Besides, it not only becomes sticky when it is used in a preparation, causing an inferior feeling of use, but also exhibits no remarkable effect in the treatment of pigmentation abnormalities, as clearly seen from an experiment described in the following. Therefore, pantetheine is disadvantageous for an external preparation for application to skin, especially as a skin-whitening agent and can hardly be used for an external preparation for application to skin. Besides, pantetheine has a very strong smell and is disadvantageous for an external preparation for application to skin even only due to this point. In contrast, pantetheine-S-sulfonic acid, as clearly seen from experiments described in the following, not only has an excellent effect in the treatment of pigmentation abnormalities but also can be prepared into an external preparation for application to skin at a far lower cost as compared to the above compounds because it is an odorless powder which can be handled easily.

This invention, relating to an external preparation for application to skin, characterized by containing pantetheine-S-sulfonic acid and/or its salt, is based on these novel findings and has been completed after confirming, from the results of further investigation, that these compounds can excellently be mixed and coexist with a base agent and other components for an external preparation for application to skin and that such a preparation can be easily prepared from these compounds.

It is also one of the great advantages of the external preparation for application to skin according to this invention that it can widely be used in various forms such as powder, solution, emulsion, ointment, cataplasm and spray. In blending pantetheine-S-sulfonic acid and/or its salt, the effective components, with a base agent for an external preparation for application to skin according to this invention, these effective components may be used alone or in combination and may be combined with another component. For example, it is also possible to use the above effective components jointly with an external antiphlogistic analgesic agent (methyl salicylate, glycyrrhiziric acid or indomethacin), an external disinfectant biocidal agent (benzalkonium chloride, thimerosal, resorcin salicylate or benzethonium chloride), an antipruritic agent (chloral hydrate, diphenhydramine or methyl salicylate), pantothenic acid or its derivative (pantothenic acid, panthenol, pantetheine or pantethine), a component extracted from vegetable or another external preparation.

In preparing the external preparation according to this invention, the conventional method generally used in preparing external preparations for application to skin can be properly used and a vehicle such as animal or vegetable fat or oil, a higher alcohol or glycol or its derivative, a surfactant, a pigment, a perfume, a stabilizer and other components suitable for the respective form of preparations can be used freely. Although there is no special restriction to the amounts of these components used in the preparation, it is usually preferred that these components be blended in a proportion of 0.1~50%.

As to the safety of pantetheine-S-sulfonic acid, since it is a sulfonic acid derivative of pantethine, which is commercially available as a bifidus factor contained in an internal medicine, the safety of which has already been confirmed, and effectively used for a serum-lipid-reducing internal medicine which has no problem in its safety, pantetheine-S-sulfonic acid can be highly safely applied to skin without causing any toxicity as well as any side effects to skin such as stimulation and itching (open patent No. 58-4721).

There is no restriction to the amount of the external preparation according to this invention to be applied to skin and the preparation should be either directly rubbed into the affected part or applied to gauze or the like before the gauze is applied on the affected part.

In the following, experiments indicating the results of the pharmacological tests (an in vitro test and actual clinical tests) of the external preparation of this invention are shown.

EXPERIMENT 1

0.25 g and 0.625 g (0.0083 mol) of calcium pantetheine-S-sulfonate respectively were dissolved in 100 ml of water to prepare test solutions (A) and (B). For comparison, pantethine solution of the same molar concentration as test solution (B) was prepared as reference solution (B) (0.43 g/100 ml). The following experiment was conducted on these test solutions and reference solution.

After 1 ml of L-tyrosine solution (0.32 g/ml), 0.1 ml of Macrbain buffer solution (pH 6.8) and 0.9 ml of each of the above test solutions and reference solution were mixed in a test tube, the mixture was incubated at 37° C. for 10 minutes. Following that, 0.1 ml of tyrosinase solution (1 mg/ml) was added to the incubated mixture before stirring, then the absorbance of the resulting mixture was measured immediately at 475 nm by means of a spectrophotometer, successively. As a blank test, the same operation as above was carried out using water instead of the above test solution or reference solution.

The results of the above experiment are shown in FIG. 1. From FIG. 1, it has been clarified that calcium pantetheine-S-sulfonate of every concentration inhibits the activity of tyrosinase while pantethine shows no tyrosinase-activity inhibiting activity at all.

EXPERIMENT 2

Each of an external preparation for application to skin according to this invention (the prescription of example 1 described in the following) and an external preparation containing ascorbic acid (an external solution containing 1% ascorbic acid) was used for seven subjects suffering from blemishes, dark skin, freckles and the like by applying the preparation to the face of each subject twice a day in the morning and in the evening for three months. The results are shown in Table 1.

TABLE 1

| Results of Pigmentation-curing Effect Test | | | | |
|---|---|---|---|---|
| | Pigmentation-curing Effect | | | |
| | Excellent | Good | No change | Inferior |
| External Preparation for Application to Skin According to This Invention | 2 | 5 | 0 | 0 |
| External Preparation Containing Ascorbic Acid | 0 | 3 | 4 | 0 |

From these results, it is seen that the external preparation of this invention has a notably higher pigmentation-curing effect as compared to the external preparation containing ascorbic acid.

EXPERIMENT 3

Variations in the luminosity difference between the pigmentation area and the non-pigmentation area were measured by use of a colorimetric color-difference meter (Nippon Denshoku CP6R-type).

This experiment was conducted on nine patients with pigmentation having liver spot by applying a creamy external preparation containing 10% of calcium pantetheine-S-sulfonate to the right or left half of the face of each patient and applying a creamy external preparation containing no calcium pantetheine-S-sulfonate to the other half on successive days twice a day in the same manner as application of cream. (A patch test was conducted beforehand to confirm the absence of any stimulating effect.)

Figure 2:
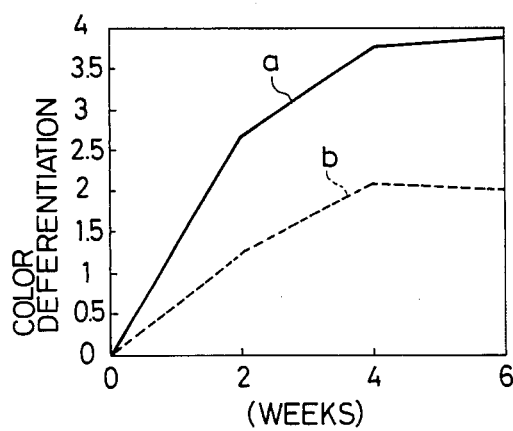

The results are shown in Table 2 and FIG. 2. Here, each value represents difference between color differences (between the non-pigmentation area and the pigmentation area) before and after the treatment and a larger value indicates a greater improvemental effect.

As clearly seen from Table 2, the above difference value successively increased due to application of the creamy external preparation containing 10% of calcium pantetheine-S-sulfonate, indicating a high improvemental effect of this preparation on liver spot. As to the mean level as well, as indicated in FIG. 2, there was an obvious difference from the creamy external preparation containing no calcium pantetheine-S-sulfonate and significant differences were found according to t-test four weeks ($P=0.035<0.05$) and six weeks ($P=0.096<0.1$) after. From these results, it has been clarified that the creamy external preparation containing 10% of calcium pantetheine-S-sulfonate is clinically very effective for the treatment of pigmentation especially liver spot.

TABLE 2

Clinical Effect of Creamy External Preparation Containing 10% of Calcium Pantetheine-S—sulfonate on Liver Spot
(Each value indicates a color difference.)

| Case No. | 10% | | | | 0% | | | |
|---|---|---|---|---|---|---|---|---|
| | 0 | Two Weeks after | Four Weeks after | Six Weeks after | 0 | Two Weeks after | Four Weeks after | Six Weeks after |
| 1 | 0.0 | 3.3 | 7.0 | 6.5 | 0.0 | 4.7 | 3.5 | 5.8 |
| 2 | 0.0 | 2.6 | 1.6 | 4.2 | 0.0 | −1.1 | −1.1 | −0.4 |
| 3 | 0.0 | 4.7 | 4.8 | | 0.0 | 3.7 | 5.0 | |
| 4 | 0.0 | 2.1 | 1.9 | 5.2 | 0.0 | 1.0 | 1.4 | 2.5 |
| 5 | 0.0 | 1.9 | | −0.5 | 0.0 | 1.4 | | 0.0 |
| 6 | 0.0 | −1.3 | | | 0.0 | −2.0 | | |
| 7 | 0.0 | 6.6 | 3.4 | | 0.0 | 2.0 | 1.6 | |
| 8 | 0.0 | 5.3 | | | 0.0 | 6.0 | | |
| 9 | 0.0 | −1.1 | | | 0.0 | 4.6 | | |
| M | 0.0 | 2.67 | 3.74 | 3.85 | 0.0 | 1.23 | 2.08 | 1.975 |

As clearly seen from the above experiments, the external preparation according to this invention has no problem in its safety to the skin and has an excellent effect in the treatment of pigmentation abnormalities in the skin (so-called "removing blemishes"). Therefore it is an excellent agent for the treatment of pigmentation abnormalities in the skin. Besides it has a good treatment effect on suntans and is an excellent skin-quality improving preparation. In addition it has remarkable curative effects on burns, wounds, frostbite, ulcers, bed sores and the like. Although further investigation is necessary in order to clarify detailed mechanisms of such effects, it is estimated that pantetheine-S-sulfonic acid has a powerful metabolism-accelerating effect.

Thus, the external preparation according to this invention causes superior effects to diseases directly hindering the maintenance of health as well as diseases indirectly hindering the maintenance of health as previously mentioned. It is just an ideal external preparation for application to skin.

Examples of this invention will be given in the following.

EXAMPLE 1

1. Ethanol: 5.0
2. Vegetable oil: 0.1
3. Polyoxyethylene hardened castor oil: 0.5
4. Propylene glycol: 5.0
5. Calcium pantetheine-S-sulfonate: 1.0
6. Antiseptic, Perfume: Proper quantity
7. Purified water: The total amount was adjusted to 100 ml.

After components 2 and 3 were dissolved in component 1, thus obtained mixture solution was dissolved in solution consisting of components 4~7 to obtain an aqueous-solution-type external preparation.

EXAMPLE 2

1. Polyvinylalcohol: 20.0
2. Ethanol: 20.0
3. Propylene Glycol: 3.0
4. Sodium pantetheine-S-sulfonate: 0.5
5. Antiseptic, Perfume: Proper quantity
6. Purified water: Total quantity was adjusted to 100 g.

After compound 1 was impregnated with compound 2, the resulting mixture was added to solution prepared by dissolving the remaining components in purified water 6 while heating and stirring to obtain solution used as a plaster-type external preparation.

EXAMPLE 3

1. Vaseline: 2.5
2. Liquid paraffin: 10.0
3. Ketostearyl alcohol: 12.0
4. Polyoxyethylene sorbitan monostearate: 7.0
5. Sorbitan monostearate: 1.0
6. Propylene glycol: 5.0
7. Calcium pantetheine-S-sulfonate: 1.0
8. Antiseptic, Perfume: Proper quantity
9. Purified water: Total quantity was adjusted to 100 g.

Oily components 1~5 and aqueous components 6, 8 and 9 were heated to 75° C. before being mixed to prepare an emulsion. Following that, component 7 was added during cooling the emulsion to 30° C. to obtain a creamy external preparation (ointment-type preparation).

EXAMPLE 4

1. Microcrystalline wax: 1.0
2. Bees wax: 2.0
3. Lanoline: 2.0
4. Liquid paraffin: 28.0
5. Sorbitan sesqui-oleate: 4.0
6. Tween 80: 1.0
7. Aluminum stearate: 0.2
8. Glycerol: 8.0
9. Sodium pantetheine-S-sulfonate: 1.0
10. Antiseptic, Perfume: Proper quantity
11. Purified water: Total quantity was adjusted to 100 g.

Oily components 1~7 and aqueous components 8, 10 and 11 were heated to 70° C. before being mixed to prepare an emulsion. Following that, component 7 was added during cooling the emulsion to 30° C. to obtain a milky external preparation.

What is claimed is:

1. A method for the treatment of pigment abnormalities on the skin of a patient comprising topically administering to the area of pigmentation abnormality an effective amount of pantetheine-S-sulfonic acid, and/or a salt thereof, represented by the following formula:

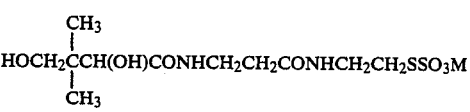

wherein M represents hydrogen, an alkali metal or ½ alkaline earth metal.

* * * * *